(12) United States Patent
Schwab et al.

(10) Patent No.: US 7,951,154 B2
(45) Date of Patent: May 31, 2011

(54) INSERTION DEVICE AND TECHNIQUES FOR ORTHOPAEDIC IMPLANTS

(75) Inventors: Frank J. Schwab, New York, NY (US); John L. White, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/800,065

(22) Filed: May 7, 2010

(65) Prior Publication Data

US 2010/0222784 A1 Sep. 2, 2010

Related U.S. Application Data

(63) Continuation of application No. 10/680,358, filed on Oct. 7, 2003, now Pat. No. 7,771,432.

(60) Provisional application No. 60/416,908, filed on Oct. 8, 2002.

(51) Int. Cl.
*A61B 17/58* (2006.01)
(52) U.S. Cl. ............................................ 606/99
(58) Field of Classification Search ................ 606/86 A, 606/99
See application file for complete search history.

(56) References Cited

U.S. PATENT DOCUMENTS

| | | | |
|---|---|---|---|
| 424,140 A | 3/1890 | Shuford |
| 3,486,505 A | 12/1969 | Morrison |
| 3,579,829 A | 5/1971 | Sampson |
| 3,848,601 A | 11/1974 | Ma et al. |
| 4,165,746 A | 8/1979 | Burgin |
| 4,386,603 A | 6/1983 | Mayfield |
| 4,502,485 A | 3/1985 | Burgin |
| 4,677,798 A | 7/1987 | Phillips |
| 4,736,738 A | 4/1988 | Lipovsek et al. |
| 4,747,588 A | 5/1988 | Dillhoff |
| 4,758,159 A | 7/1988 | Weissman |
| 4,898,161 A | 2/1990 | Grundei |
| 4,955,885 A | 9/1990 | Meyers |
| 5,052,373 A | 10/1991 | Michelson |
| 5,088,472 A | 2/1992 | Fakhrai |
| 5,122,130 A | 6/1992 | Keller |
| 5,192,327 A | 3/1993 | Brantigan |
| 5,235,966 A | 8/1993 | Jamner |
| 5,431,658 A | 7/1995 | Moskovich |
| 5,505,732 A | 4/1996 | Michelson |
| 5,571,109 A | 11/1996 | Bertagnoli |
| 5,599,279 A | 2/1997 | Slotman et al. |
| 5,616,117 A | 4/1997 | Dinkler et al. |
| 5,697,889 A | 12/1997 | Slotman et al. |
| 5,722,977 A | 3/1998 | Wilhelmy |

(Continued)

FOREIGN PATENT DOCUMENTS

DE 29703850 U1 6/1997

(Continued)

OTHER PUBLICATIONS

Synthes, SynCage Surgical Technique; Mathys Medical Ltd—Osteosynthesis; pp. 1-24; Guterstrasse 5, PO Box CH-2544, Bettlach, Switzerland.

*Primary Examiner* — Thomas C Barrett
*Assistant Examiner* — Nicholas Woodall (57) ABSTRACT

Instruments for inserting an implant in a space between adjacent bony portions include a pair of parallel guide members extending distally from a proximal frame portion. Tamps and impaction instruments facilitate advancement of the implant between the guide members to the space between the adjacent bony portions.

12 Claims, 6 Drawing Sheets

U.S. PATENT DOCUMENTS

| | | | |
|---|---|---|---|
| 5,944,658 | A | 8/1999 | Koros et al. |
| 6,004,326 | A | 12/1999 | Castro et al. |
| 6,096,038 | A | 8/2000 | Michelson |
| 6,139,493 | A | 10/2000 | Koros et al. |
| 6,159,215 | A | 12/2000 | Urbahns et al. |
| 6,174,311 | B1 | 1/2001 | Branch et al. |
| 6,179,873 | B1 | 1/2001 | Zientek |
| 6,224,599 | B1 | 5/2001 | Baynham et al. |
| 6,224,607 | B1 | 5/2001 | Michelson |
| 6,261,296 | B1 | 7/2001 | Aebi et al. |
| 6,270,498 | B1 | 8/2001 | Michelson |
| 6,332,887 | B1 | 12/2001 | Knox |
| 6,395,034 | B1 | 5/2002 | Suddaby |
| 6,436,101 | B1 | 8/2002 | Hamada |
| 6,478,800 | B1 | 11/2002 | Fraser et al. |
| 6,514,260 | B1 | 2/2003 | Zdeblick et al. |
| 6,565,574 | B2 | 5/2003 | Michelson |
| 6,569,168 | B2 | 5/2003 | Lin |
| 6,585,749 | B2 | 7/2003 | Hanson |
| 6,595,995 | B2 | 7/2003 | Zdeblick et al. |
| 6,599,294 | B2 | 7/2003 | Fuss et al. |
| 6,610,065 | B1 | 8/2003 | Branch et al. |
| 6,635,060 | B2 | 10/2003 | Hanson et al. |
| 6,641,582 | B1 | 11/2003 | Hanson et al. |
| 6,648,891 | B2 | 11/2003 | Kim |
| 6,652,533 | B2 | 11/2003 | O'Neil |
| 6,663,638 | B2 | 12/2003 | Ralph et al. |
| 6,830,570 | B1 | 12/2004 | Frey et al. |
| 7,118,580 | B1 | 10/2006 | Beyersdorff et al. |
| 7,169,153 | B2 | 1/2007 | Keller |
| 2001/0010001 | A1 | 7/2001 | Michelson |
| 2002/0016592 | A1 | 2/2002 | Branch et al. |
| 2002/0045904 | A1 | 4/2002 | Fuss et al. |
| 2002/0058950 | A1 | 5/2002 | Winterbottom et al. |
| 2002/0082695 | A1 | 6/2002 | Neumann |
| 2002/0116009 | A1 | 8/2002 | Fraser et al. |
| 2002/0138078 | A1 | 9/2002 | Chappuis |
| 2002/0177897 | A1 | 11/2002 | Michelson |
| 2003/0028197 | A1 | 2/2003 | Hanson et al. |
| 2003/0045884 | A1 | 3/2003 | Robie et al. |
| 2003/0069586 | A1 | 4/2003 | Errico et al. |
| 2003/0078590 | A1 | 4/2003 | Errico et al. |
| 2003/0083664 | A1 | 5/2003 | Rogers et al. |
| 2003/0130737 | A1 | 7/2003 | McGahan et al. |
| 2003/0149438 | A1 | 8/2003 | Nichols et al. |
| 2003/0187448 | A1 | 10/2003 | Michelson |
| 2003/0195517 | A1 | 10/2003 | Michelson |
| 2003/0195520 | A1 | 10/2003 | Boyd et al. |
| 2003/0229358 | A1 | 12/2003 | Errico et al. |
| 2004/0002758 | A1 | 1/2004 | Landry et al. |
| 2004/0024291 | A1 | 2/2004 | Zinkel |
| 2004/0225295 | A1 | 11/2004 | Zubok et al. |
| 2004/0230191 | A1 | 11/2004 | Frey et al. |
| 2005/0021040 | A1 | 1/2005 | Bertagnoli |
| 2005/0075643 | A1 | 4/2005 | Schwab et al. |
| 2005/0143747 | A1 | 6/2005 | Zubok et al. |

FOREIGN PATENT DOCUMENTS

| | | |
|---|---|---|
| EP | 0531710 A2 | 3/1993 |
| EP | 0637439 A1 | 2/1995 |
| EP | 1295578 A2 | 3/2003 |
| EP | 1323396 A2 | 7/2003 |

INSERTION DEVICE AND TECHNIQUES FOR ORTHOPAEDIC IMPLANTS

CROSS-REFERENCE TO RELATED APPLICATIONS

This application is a continuation of U.S. patent app. Ser. No. 10/680,358 filed on Oct. 7, 2003, now U.S. Pat. No. 7,771,432 which claims the benefit of the filing date of Provisional Application Ser. No. 60/416,908, filed Oct. 8, 2002, each of which is incorporated herein by reference in its entirety.

BACKGROUND

The repair and reconstruction of bony structures is sometimes accomplished by directly fixing adjacent bony portions to each other, such as by a plate. In other instances, bone growth inducing material can be introduced between the adjacent bony portions, which over time results in a solid bony connection. In some instances, the adjacent bony portions are not sufficiently strong to maintain their patency as the bone heals or the bone grows between the adjacent structures through the bone growth inducing material. In these instances, mesh structures, cages and other implants have been provided to engage the adjacent bony structures to provide additional stability.

One problem, among others, with such implants is associated with positioning the implant between adjacent bony portions. Insertion can be difficult or time consuming if the bony portions are spaced too close together, or if the adjacent tissue, nerves or vasculature impedes access to or placement of the implant in the space between the bony portions.

SUMMARY

The invention provides instruments that facilitate placement of an implant between adjacent bony portions.

According to one aspect, an instrument for inserting an implant includes a proximal portion with a frame and a distal portion with first and second guide members extending distally from the frame. The first and second guide members each include opposite first and second sides extending between a proximal end and a distal end; a guide surface extending from the proximal to the distal end between the first and second sides; and a guide flange extending along only one of the first and second sides, the guide flange projecting from the guide surface of the corresponding one of the first and second guide members toward the guide surface of the other of said first and second guide members.

According to another aspect, an instrument for inserting an instrument includes a proximal portion with a frame having a stationary arm and a movable arm coupled to the stationary arm. The instrument includes a distal portion with a first guide member extending distally from the movable arm and a second guide member extending distally from the stationary arm. The first and second guide members each include a guide surface oriented toward the guide surface of the other of the first and second guide members. The first and second guide members being movable toward and away from one another by moving the movable arm relative to the stationary arm.

According to a further aspect, an instrument for inserting an implant includes a distal portion with a first guide member and a second guide member extending along the first guide member. The first and second guide members each include a guide surface oriented toward and generally parallel to the guide surface of the other of the first and second guide members. A proximal portion of the instrument includes a frame coupled to the first and second guide members. The frame is structured to move the first and second guide members toward and away from one another with the guide surfaces remaining generally parallel.

According to another aspect, an instrument for inserting an implant in a space between adjacent bony portions includes a first member and a second member each extending between a distal end a proximal end. The second member is coupled with the first member and movable relative thereto to removably grip an implant between the distal ends of the first and second members. The proximal end of one of the first and second members extends further proximally than the proximal end of the other of the first and second members to an impaction head for receiving an impaction force to facilitate insertion of the implant into the space between adjacent bony portions.

According to a further aspect, an instrument for tamping a tapered implant into a space between adjacent bony portions includes a proximal portion with a shaft and a distal portion with a head. The head includes a body and a wedge member. The body includes a distal end surface to deliver a tamping force to the tapered implant positioned thereagainst. The wedge member extends distally from the end surface of the body and is positionable along an adjacent tapered end surface of the tapered implant when the distal end surface is positioned adjacent to the tapered implant. The wedge member forms a temporary surface along the tapered end surface that is substantially parallel to a second surface of the tapered implant opposite the tapered surface.

These and other aspects can be discerned from the following written description and accompanying figures.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

An instrument is provided for inserting implants and other devices into a space between adjacent bony portions to support the adjacent bony portions. The inserter instrument can be used with current mesh or cage-type devices for engagement with adjacent bony portions, although use with other types of bone supporting devices is also contemplated. The inserter instrument can have application in spinal surgical procedures for inserting an implant in the disc space between adjacent vertebrae. In the illustrated embodiments of FIGS. 1-4, the adjacent bony portions include first vertebra 140 and second vertebra 142. The vertebrae 140, 142 include a disc space 144 therebetween, which provides a space for insertion of an implant between the adjacent bony portions. The inserter instrument can also be used in corpectomy procedures to position an implant between adjacent vertebrae on either side of one or more removed or partially removed vertebral bodies. The inserter instrument can be used in various approaches to the spine, including posterior, posterior lateral, transforaminal, lateral, anterior lateral, and anterior approaches. It is contemplated that the inserter instrument can have application in surgical procedures other than spinal surgical procedures to facilitate insertion of an implant between adjacent bony portions.

In FIGS. 1-4, an inserter instrument 20 is shown. Inserter instrument 20 includes a proximal frame portion 22 and a distal portion 24. Distal portion 24 can be provided with a pair of guide members 70, 90 to guide placement of an implant into a space between adjacent bony portions. Guide members 70, 90 can also be moved via proximal frame portion 22 to provide a desired spacing between the adjacent bony portions and/or the guide members 70, 90. Proximal frame portion 22 can provide for remote movement and repositioning of distal portion 24 with guide members 70, 90 positioned in alignment with the space between adjacent bony portions. Proximal frame portion 22 can also releasably maintain distal portion 24 in the desired position. Inserter instrument 20 can be used to access the space between adjacent bony portions in an open or minimally invasive procedure. Additionally, proximal frame portion 22 can be provided with an adjustment mechanism 38 to effect an adjustment of the spacing between guide members 70, 90 of distal portion 24.

Proximal frame portion 22 can include any device or mechanism capable of adjusting the position or spacing of distal portion 24. Proximal frame portion 22 may include linkage systems, wire systems, gear systems, and flexible adjustment systems, for example. Proximal frame portion 22 may include linear and/or rotationally moving elements. Proximal frame portion 22 may be permanently fixed to distal portion 24, removably fixed to distal portion 24, or a combination of permanent and removable fixation. Suitable examples of proximal frame portion 22 components include solid shaft like elements, bar stock, tubular elements, rod-like elements, linkages, elastically-deformable members, and articulating connectors, for example. Adjustment mechanism 38 of proximal frame portion 22 can position and/or maintain distal portion 24 in any one of a number of relative positions between guide members 70, 90, and is provided with means for securing one or more components of distal portion 24 in a particular position.

Distal portion 24 can include a pair of guide members 70, 90 movable away from and toward one another by adjustment mechanism 38 to spread or contact adjacent bony structures. Guide members 70, 90 can be coupled to proximal frame portion 22 for movement in parallel relation to one another, although non-parallel movement is also contemplated. Distal portion 24 can include a low profile arrangement for insertion of guide members 70, 90 into a space between the adjacent bony portions. Guide members 70, 90 can include means for engaging the bony structure to resist movement of the spreading members relative to the bony structure. Such engagement means includes pitting, knurling, serrations, teeth, ridges, barbs, spikes, peeks and valleys, and grooves, for example.

Guide members 70, 90 extend distally from proximal frame portion 22, and define a path for insertion of an implant between the adjacent bony portions, such as vertebrae 140, 142. Guide member 70 includes a body 76 extending from a proximal end 72 to a distal end 74. Body 76 can be provided with a guide flange 78 along one side thereof. A guide surface 80 extends along body 76 between proximal end 72 and distal end 74. Similarly, guide member 90 includes a body 96 extending from a proximal end 92 to a distal end 94. Body 96 can be provided with a guide flange 98 along one side thereof positioned opposite of guide flange 78. A guide surface 100 extends along body 96 and is oriented toward guide surface 80, forming a guide path therebetween for receiving an implant, such as implant 120. Guide surface 100 extends between proximal end 92 and distal end 94.

Distal end 74 of guide member 70 can be provided with an abutment member 82 extending therefrom opposite of guide surface 80 for contacting the adjacent bony structure to limit the insertion depth of guide member 70 into the space between the adjacent bony portions. A support member 84 extends distally from abutment member 82 and into the space between the adjacent bony portions, forming an extension of guide surface 80. Distal end 94 of guide member 90 can be provided with an abutment member 102 extending therefrom for contacting the adjacent bony portion to limit the insertion depth of guide member 90 into the space between the adjacent bony portions. A support member 104 extends distally from abutment member 102 and into the space between the adjacent bony portions, forming an extension of guide surface 100.

Support members 84, 104 can extend along an adjacent surface of the adjacent bony portion to facilitate insertion of the implant 120 into the space between the adjacent bony portions. Support members 84, 104 also contact the adjacent bony portions to distribute a spreading or distraction force thereto. The spreading or distraction force can be applied to the adjacent bony portions by separating guide members 70, 90 through manipulation of proximal frame portion 22. Support members 84, 104 further protect the adjacent vertebral endplate as implant 120 is positioned in the space between the adjacent bony portions. Support member 84, 104 can prevent implant 120 from cutting into or becoming engaged with bony structure at the entrance into the space therebetween, and facilitating insertion of implant 120 in the desired position in the space between the adjacent bony portions.

Figure 3:
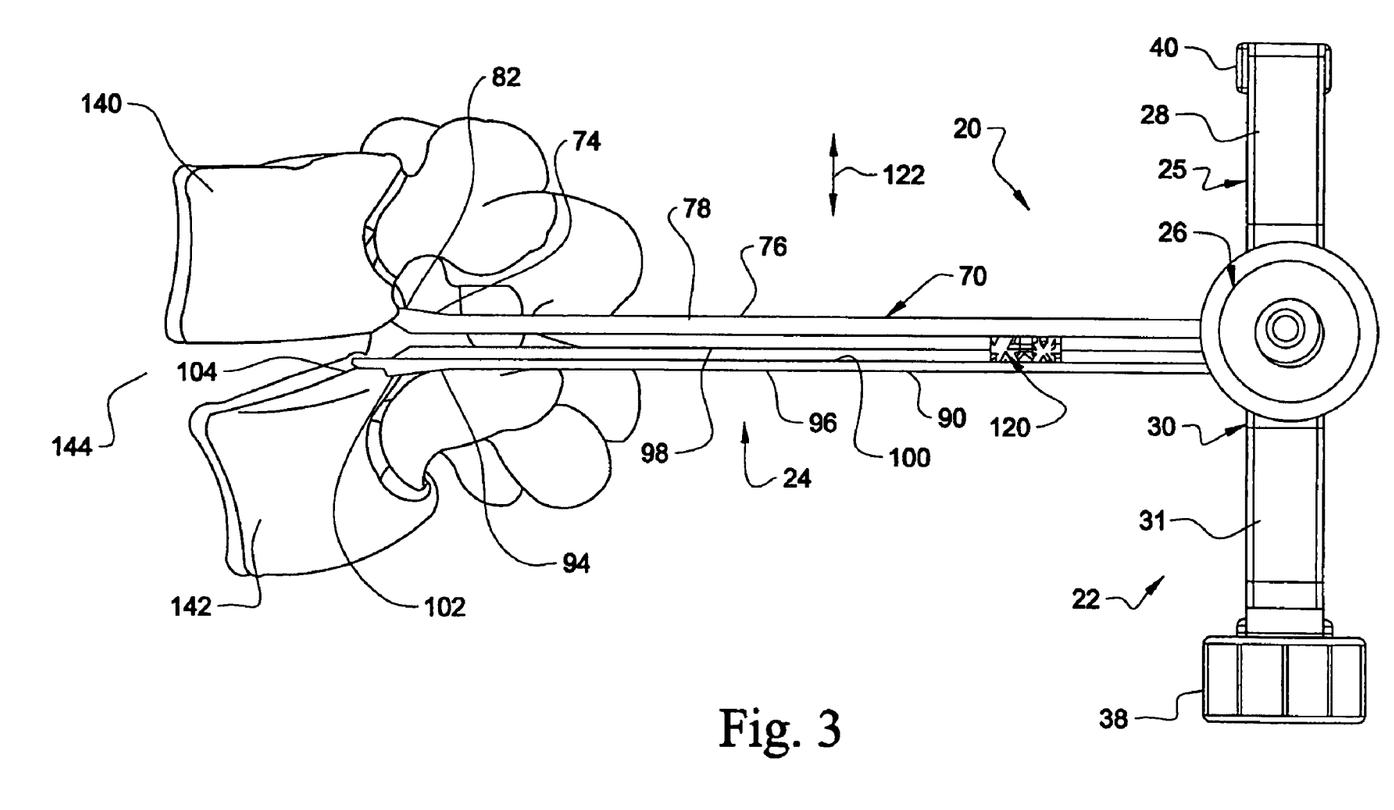
FIG. 3 is an elevational view of the implant inserter instrument positioned adjacent the spinal column segment guiding an implant to a space between adjacent vertebrae.

As implant 120 is guided between guide members 70, 90 into the space between the adjacent bony portions, the positioning of implant 120 is controlled in the cephalad/caudal directions, as indicated by arrows 122 (FIG. 3), by contact of the guide surfaces 80, 100 with the implant 120. Guide surfaces 80, 100 align implant 120 with the space between the adjacent bony portions. The lateral positioning of implant 120 along guide members 70, 90 is controlled by guide flanges 78, 98 so that implant 120 does not slip out from between guide members 70, 90 where it might contact or damage tissue, nerves, vasculature or other tissue structures adjacent the bony portions on the approach to the space therebetween. Furthermore, frame portion 22 is configured so that guide members 70, 90 are substantially unobstructed at their proximal ends, as shown in FIG. 3, permitting implant 120 to be readily positioned therebetween even when the distal portions of guide members 70, 90 are in the disc space.

Guide flange 78 extends toward guide member 90 and projects beyond guide surface 80 to form a wall therealong. Similarly, guide flange 98 extends toward guide member 70 and projects beyond guide surface 100 to form a wall therealong. Guide flange 98 is located on the side of guide member 90 opposite guide flange 78. By positioning guide flanges 78, 98 only along opposite sides of guide members 70, 90, additional space is provided between guide members 70, 90 for the surgeon to access implant 120 with a tool or the like as it is advanced along guide members 70, 90. For example, the upper and lower surfaces of the implant can be visualized when it is positioned between guide members 70, 90. Guide flanges 78, 98 control lateral movement of implant 120 with respect to guide members 70, 90 therebetween. Guide flanges 78, 98 terminate at the distal ends 74, 94 of guide members 70, 90 such that guide flanges 78, 98 do not extend along support members 84, 104. Accordingly, implant 120 can be moved laterally relative to guide members 70, 90 along support members 84, 104 in the space between the adjacent bony portions to place the implant in the desired position in the space.

In the illustrated embodiment of inserter instrument 20, proximal frame portion 22 includes a handle 26 coupled to a frame 25. Frame 25 includes a stationary arm 30 that includes a general J-shape. Stationary arm 30 includes a first portion 31 extending from handle 26. Stationary arm includes a first lateral extension 50 extending from an end of first portion 31 and away from handle 26. First lateral extension 50 further includes a first vertical extension 52 extending from an end thereof opposite first portion 31 that is generally parallel first portion 31. A first hand-hole 56 is provided through first lateral extension 50. Stationary arm 30 further includes a second portion 28 extending from handle 26 in a direction opposite first portion 31. Second portion 28 defines a receptacle 29.

Frame 25 further includes mobile arm 32 having a first end portion 34 positioned in receptacle 29. First end portion 34 can be captured in receptacle 29 such that mobile arm 32 is constrained to move along second portion 28 in the directions indicated by arrows 56. Mobile arm 32 includes a second lateral extension 37 extending from first end portion 34 in a direction generally parallel to first lateral extension 50. Mobile arm 32 further includes a second vertical extension 36 extending generally parallel to first portion 28. A second hand-hole 42 is formed through second lateral extension 37.

Figure 4:
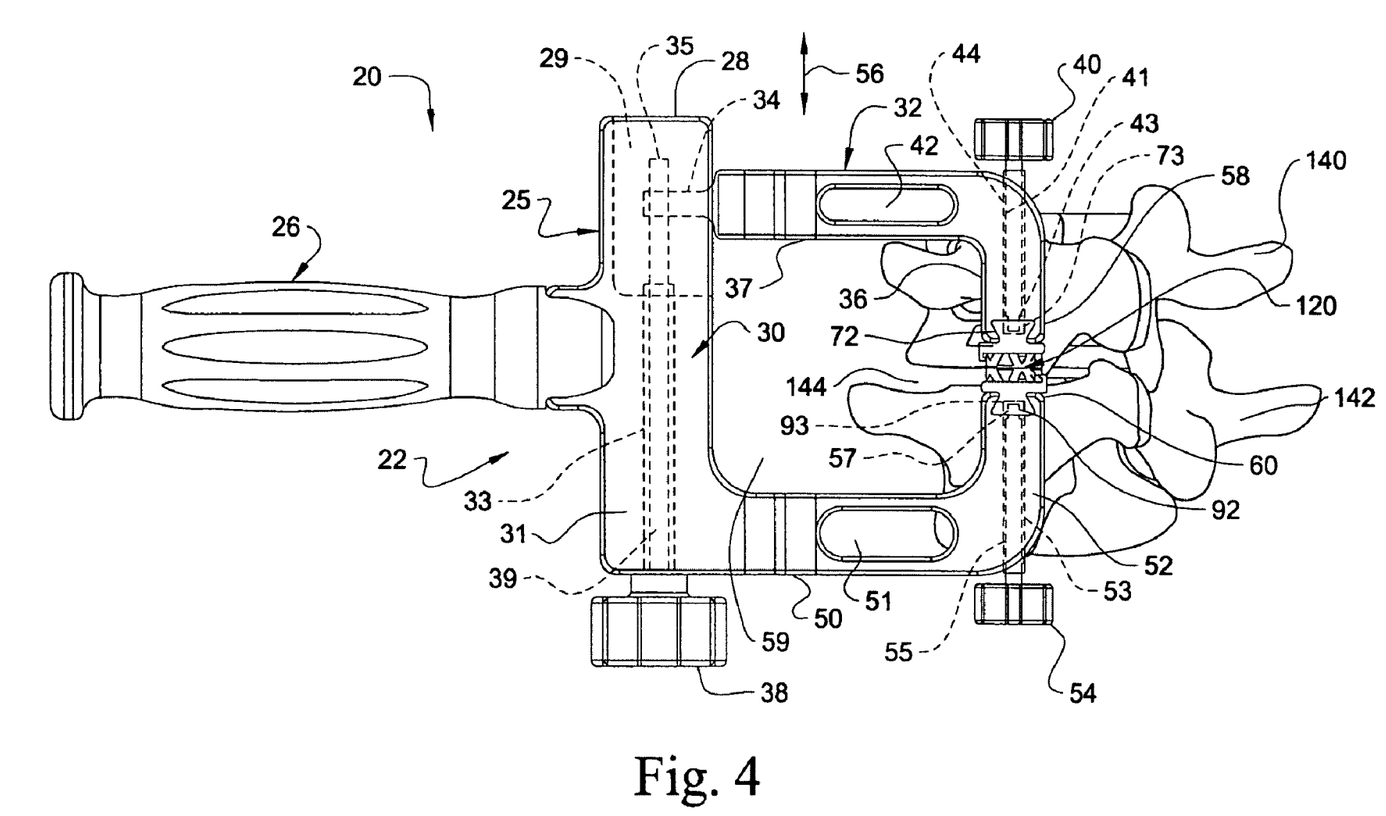
FIG. 4 is another elevational view of the implant inserter instrument guiding the implant to the space between adjacent vertebrae of the spinal column segment.

Frame 25 further includes an adjustment mechanism 38 extending through stationary arm 30 and engaged with first end portion 34 of mobile arm 32, as shown in FIG. 4. Adjustment mechanism 38 can be manipulated with a hand knob or other hand or tool engaging structure to move mobile arm 32 relative to stationary arm 30 in receptacle 29 in the directions indicated by arrows 56. Adjustment mechanism 38 includes a shaft 39 that is captured in a passage 33 extending through first portion 31 and in communication with receptacle 29. Shaft 39 includes a distal end portion 35 threadingly engaged with first end portion 34 of mobile arm 32. As shaft 39 is rotated in passage 33, mobile arm 32 is moved in a corresponding one of the directions indicated by arrows 56 relative to stationary arm 30, thereby effecting movement of guide member 70 relative to guide member 90. Accordingly, the spacing between guide surfaces 80, 100 can be adjusted to accommodate the height of the implant to be guided therebetween, and/or to adjust the spacing between the adjacent bony portions. Mobile arm 32 can be disengaged from stationary arm 30 by rotating shaft 39 sufficiently to translate mobile arm 32 away from stationary arm 30 to disengage first end portion 34 from distal end portion 35 of shaft 39.

Instrument 20 includes guide members 70, 90 extending distally from proximal frame portion 22. In the illustrated embodiment, guide member 70 includes proximal end 72 coupled to second vertical portion 36 of mobile arm 32, and guide member 90 includes proximal end 92 coupled to first vertical portion 52 of stationary arm 30. Various means for coupling guide members 70 and 90 to the respective vertical portions 36, 52 are contemplated.

Figure 1:
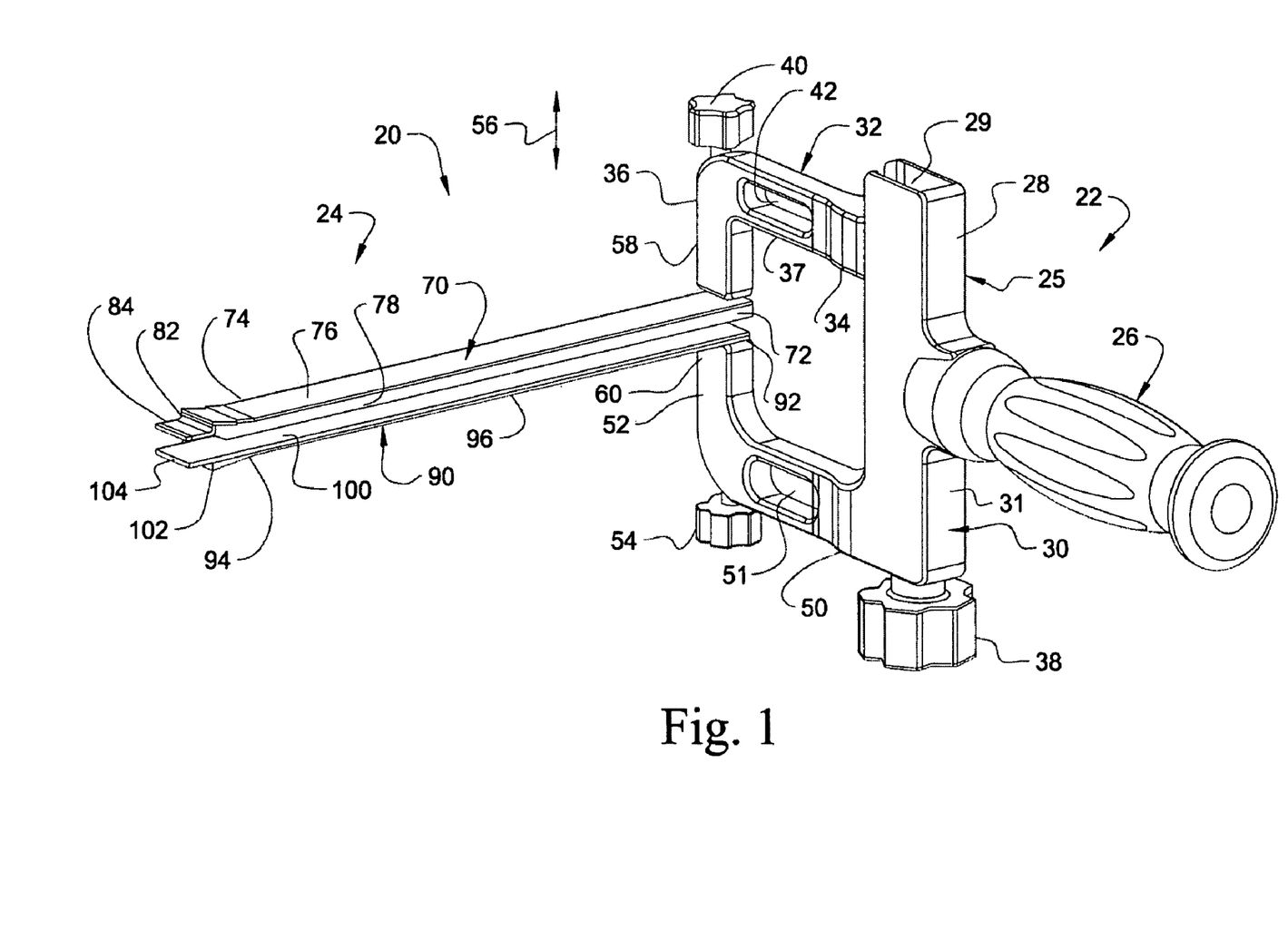
FIG. 1 is a perspective view of an implant inserter instrument.
Figure 2:
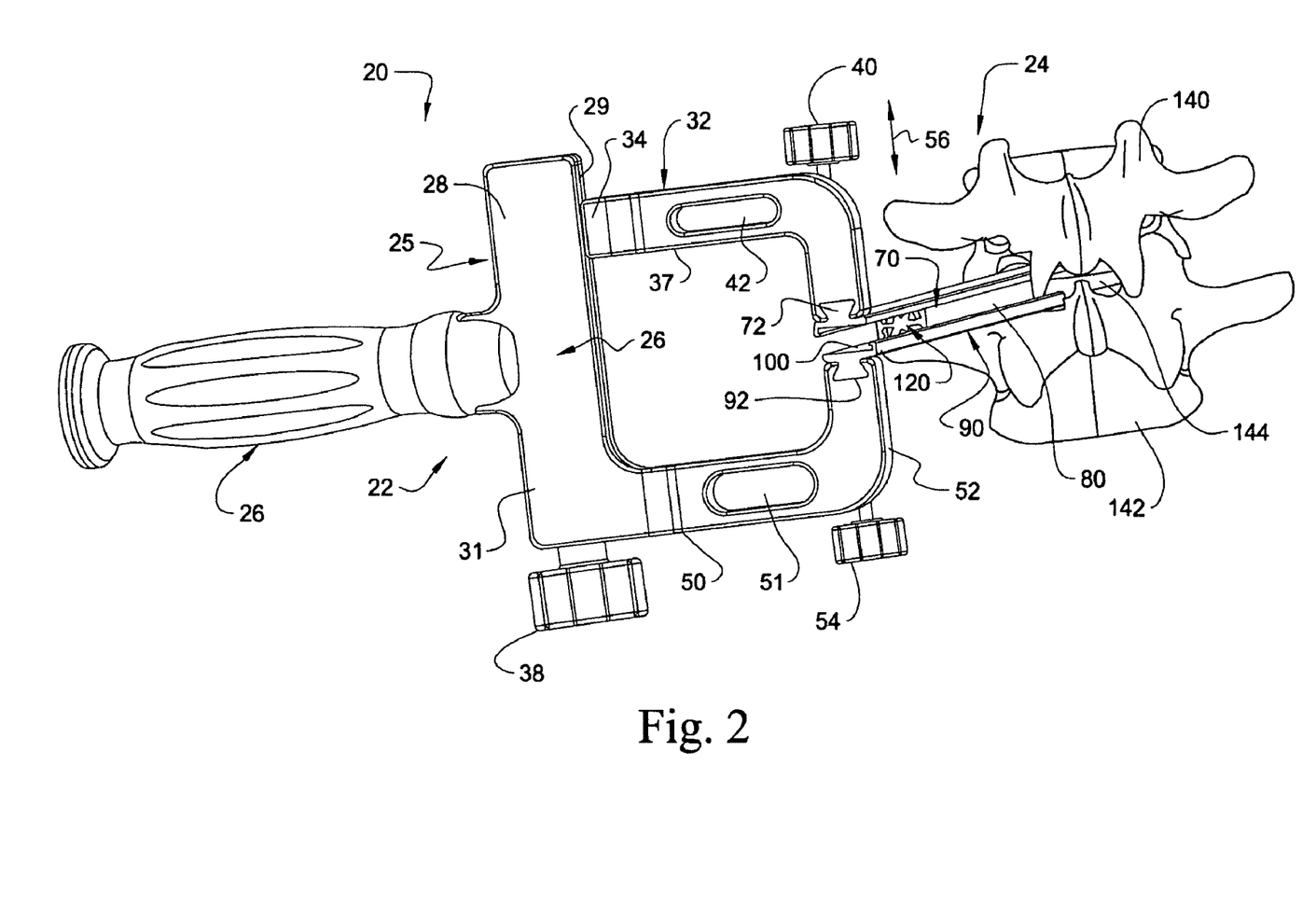
FIG. 2 is a perspective view of the implant inserter instrument positioned adjacent a spinal column segment with an implant being guided to a space between adjacent vertebrae.

In the illustrated embodiment such as shown in FIG. 4, proximal end 72 of guide member 70 has a dovetail configuration that is slidingly received in a correspondingly shaped receptacle in end 58 of second vertical portion 36. The dovetail receptacle opens toward the side of vertical portion 36 facing away from the direction in which guide members 70, 90 extend, as shown in FIG. 4, and is closed on the side of vertical arm portion 36 from which guide members 70, 90 extend, as shown in FIG. 1. A coupling mechanism 40 can include a shaft 41 extending from the illustrated hand knob that extends through a passage 37 in second vertical portion 36. A distal end 43 of shaft 41 can engage a receptacle or recess 73 in proximal end 72 of guide member 70 in an interference fit to prevent guide member 70 from moving relative second vertical portion 36 toward the open side of the dovetail receptacle. In one embodiment, shaft 41 of coupling mechanism 40 can be threadingly engaged in passage 37 extending through second vertical portion 36 and translate relative thereto to engage and disengage guide member 70. Other embodiments contemplate that shaft 41 of coupling mechanism 40 could include a threaded distal end 43 that engages a threaded receptacle 73 in proximal end 72 of guide member 70.

Second guide member 90 can similarly be coupled to stationary arm 30 with coupling mechanism 54 such as discussed above with respect to first guide member 70 and coupling mechanism 40. Coupling mechanism 54 can be provided with a shaft 55 in a passage 53 of first vertical portion 52. Shaft 55 includes a distal end 57 received in a receptacle or recess 93 formed in proximal end 92 of second guide member 90.

The transverse orientation of proximal portion 22 relative to distal portion 24 facilitates viewing at the distal end of inserter instrument 20. This viewing capability is further enhanced by the vertical portions of stationary arm 30 and mobile arm 32, which along with the lateral extensions define an opening 59 therebetween that facilitates viewing and access of the surgical space by the surgeon through frame 25. Opening 59 can be C-shaped. Other shapes are also contemplated, including round, oval, non-circular shapes that include an open side formed at guide members 70, 90. Hand-holes 42, 56 and handle 26 can be grasped by the surgeon to facilitate manual repositioning or removal of inserter instrument 20 relative to the adjacent bony portions. Manipulation is facilitated by providing handle 26 in a plane extending between guide members 70, 90, and by further positioning hand-holes 42, 56 along the lateral extension 37, 50.

Figure 5:
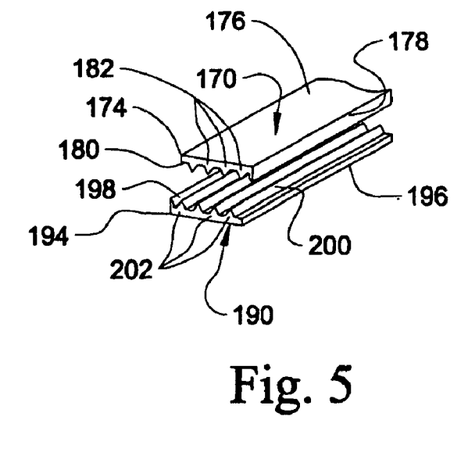
FIG. 5 is a perspective view of a distal portion of another embodiment pair of guide members for an implant inserter instrument.

In FIG. 5 there is shown another embodiment for the guide members designated as guide members 170, 190. Only the distal portions of guide members 170, 190 are shown. Guide member 170 includes a body 176 having a lateral guide flange 178 and a guide surface 180. A number of guide rails 182 are provided along guide surface 180. An abutment member, although not shown, could also be provided. Guide member 190 includes a body 196 having a lateral guide flange 198 and a guide surface 200. A number of guide rails 202 are provided along guide surface 200. An abutment member, although not shown, could also be provided. Guide rails 182, 202 can interfit with teeth, recesses or other surface features provided along the upper and lower surfaces of the implant or implant insertion instrument to prevent the implant from rotating as it is advanced along guide surfaces 180, 200. In the illustrated embodiment, guide rails 182, 202 are formed by V-shaped recesses; however, other forms and shapes for guide rails 182, 202 are also contemplated.

In one application, it is contemplated that the implants discussed herein could be mesh type cages such as those provided in U.S. Pat. No. 5,897,556 to Drewry et al., which is incorporated herein by reference in its entirety. Guide rails 182, 202 could be spaced and configured to be received in recesses provided at the upper and lower ends of the cage described in the '556 patent. Other embodiments contemplate the guide rails could interdigitate with grooves formed along upper and lower surfaces of the implant.

Figure 6:
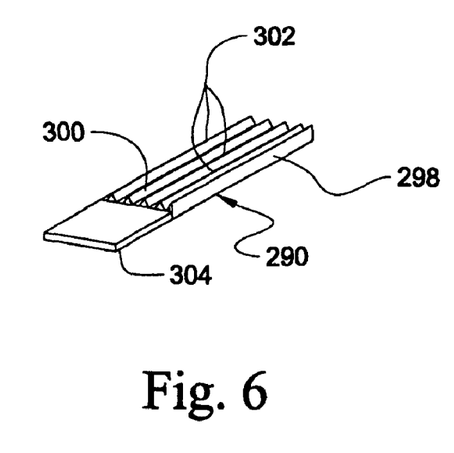
FIG. 6 is a perspective view of a distal portion of another embodiment guide member for an implant inserter instrument.

In FIG. 6, another embodiment guide member 290 is shown, which is similar to guide member 190 but includes a support member 304 extending distally from guide surface 300. Guide surface 300 includes a number of guide rails 302 that terminate at the proximal end of support member 304. Guide member 290 includes a lateral guide flange 298 extending therealong. It should be understood that a similar guide member can extend along guide member 290 and provide an upper guide surface such as shown above with respect to guide members 70, 90.

Figure 7:
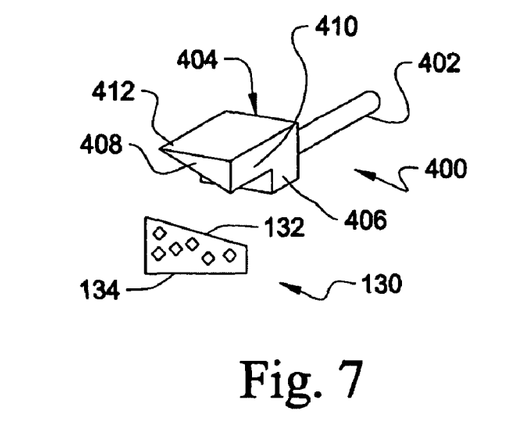
FIG. 7 is a perspective view of an implant tamping instrument and a tapered implant.

Referring now to FIG. 7, there is shown a tamping instrument 400 configured to push an implant 130 between a pair of guide members of an inserter instrument, and into position between adjacent bony portions, such as adjacent vertebrae of a spinal column. Tamping instrument 400 includes a proximal shaft and handle 402 and a distal head 404. Head 404 includes a body 406 positionable against a sidewall of the implant 130 to deliver a tamping or pushing force thereto.

Head 404 further includes a wedge member 408 positionable along a tapered or obliquely oriented upper or lower surface of the implant 130, such as upper surface 132. Wedge member 408 provides a temporary upper surface that is parallel to lower surface 134 of implant 130, or vice versa. This allows tapered implant 130 to be guided to the space between adjacent bony portions by a pair of generally parallel guide members, such as guide members 70, 90 of inserter instrument 20. Wedge member 408 includes a thickness that is tapered from a first side 410 along a corresponding first side of body 406 to a second side 412 along a corresponding second side of body 406. Wedge member 408 is tapered transversely to an axis along which the implant is inserted into the space between adjacent bony portions. Wedge member 408 is adapted for inserting a tapered implant from a lateral approach to a spinal column segment in which angulation between the vertebral endplates is desired.

Figure 8:
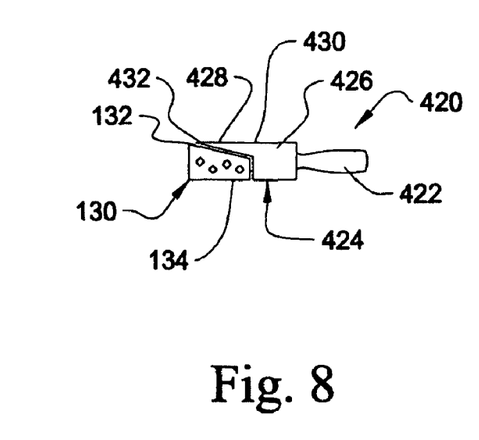
FIG. 8 is an elevational view of another embodiment implant tamping instrument and a tapered implant.

Wedge member 408 could also be tapered in thickness to accommodate insertion of a tapered implant from other approaches, including oblique approaches, posterior-lateral approaches, anterior-lateral approaches, and anterior approaches. For example, in FIG. 8 another embodiment tamping instrument 420 is shown that is adapted to, for example, insert a tapered implant 130 between guide members 70, 90 from a posterior approach to provide lordotic curvature between endplates of adjacent vertebrae. Tamping instrument 420 includes a shaft and handle 422 and a head 424. Head 424 includes a body 426 and a wedge member 428 extending distally from body 426. Wedge member 428 tapers from a proximal end 430 at body 426 to a distal end 432. Wedge member 428 provides implant 130 with a temporary upper surface that is parallel to lower surface 134, or vice versa.

Figure 9:
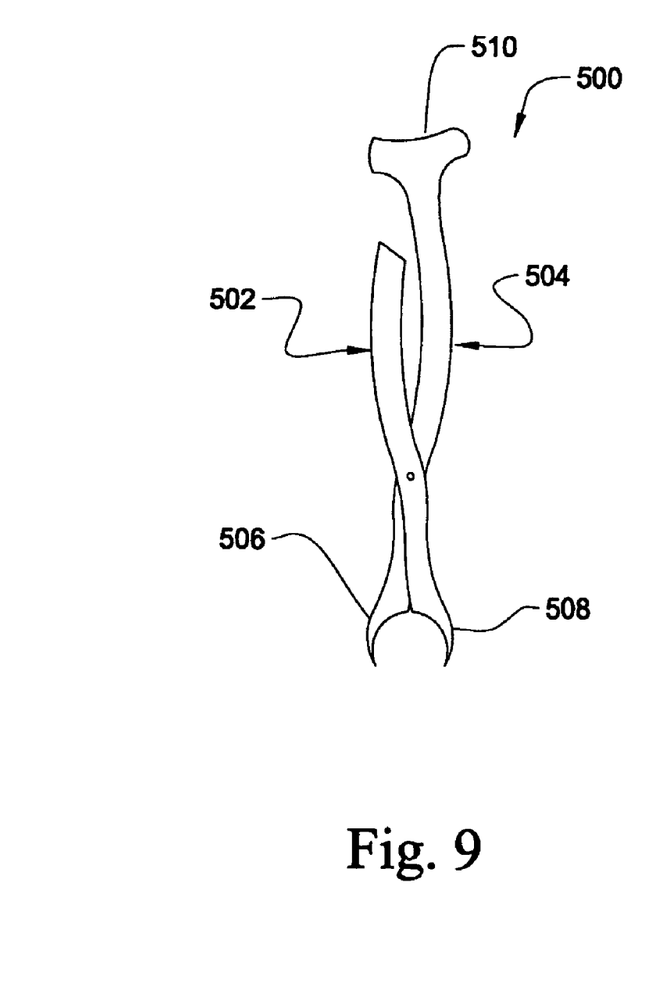
FIG. 9 is an elevational view of an implant holder.
Figure 10:
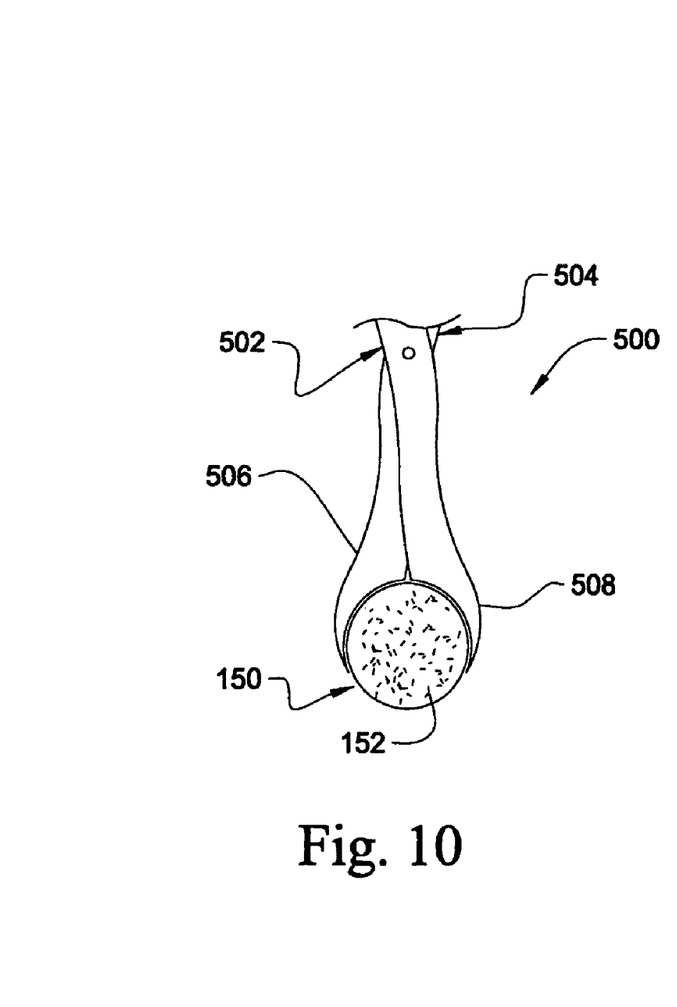
FIG. 10 is an elevational view of a distal end portion of the implant holder of FIG. 9 holding an implant.

Referring now to FIGS. 9 and 10, there is shown an implant holder 500 configured to hold an implant during insertion between, for example, guide members 70, 90 to the space between the adjacent bony portions. Implant holder 500 includes a first arm 502 pivotally coupled to a second arm 504. Second arm 504 includes a distal end portion 506 configured to receive a portion of an implant, such as implant 150, therein. Similarly, first arm 502 includes a distal end portion 508 configured to receive a portion of implant 150 therein. In the illustrated embodiment, implant 150 has a circular outer surface profile, and distal end portions 506, 508 have a concave surface profile adapted to receive implant 150 therealong. To facilitate advancement of implant 150 between guide members 70, 90, second arm 504 can include a proximal extension 510 that is configured to receive an impaction force from the hand, hammer, or other instrument. Proximal extension 510 can extend proximally further than first arm 502, and can be enlarged to distribute the impaction force over a greater area. It should be understood that arms 502, 504 could be configured to grip an implant of any shape.

The implant discussed herein can be fusion implants adapted to permit fusion of the adjacent bony portions. Such fusion implants can be packed with bone growth promoting material and/or therapeutic agents, such as bone growth material 152 in implant 150. The implants discussed herein can also by interbody spacers, artificial disc components or devices, or other implant desired to be positioned between adjacent bony portions.

The instruments discussed herein can protect the adjacent tissue and vasculature from the implant during insertion by preventing the implant from twisting and moving outside the guide path during insertion. The instruments can also protect the adjacent bony portions while guiding the implant across the adjacent bony portions during insertion to a desired position between the adjacent bony portions. Visualization of implant insertion is enhanced with embodiments including a proximal frame portion adapted to facilitate viewing. Furthermore, the instruments can be adapted to guide insertion of implants of various heights and various taper angles, and to provide varying spacing between adjacent bony portions, while maintaining generally parallel guide surfaces. The instruments also permit loading of implants between parallel guide members through a proximal end opening between the guide members.

While the invention has been illustrated and described in detail in the drawings and foregoing description, the same is to be considered as illustrative and not restrictive in character. All changes and modifications that come within the spirit of the invention are desired to be protected.

What is claimed is:

1. An instrument and implant assembly, comprising:
   an insertion instrument including:
      a proximal portion including a frame;
      a distal portion including first and second guide members mounted to and extending distally from said frame, said first and second guide members are each elongated in a direction extending along a first and an opposite second side thereof, said first and second sides extending between a proximal end and a distal end of said respective guide member, wherein said first sides are aligned with one another and said second sides are aligned with one another, each of said first and second guide members further including a guide surface extending between said proximal end and said distal end thereof, said first guide member including a guide flange on said first side of said first guide member with said guide flange on said first side projecting from said guide surface of said first guide member toward said second guide member and said second guide member includes a guide flange on said second side of said second guide member projecting from said guide surface of said second guide member toward said first guide member, wherein said first and second guide members include only one guide flange along said first and second sides thereof, respectively, so that said guide flanges are located on opposite sides of said first and second guide members; and a spinal implant including a first width transverse to an insertion direction along which said spinal implant is advanced between said first and second guide members toward vertebrae of a spinal column, wherein said guide surfaces of said first and second guide members each include a second width between said first and second sides thereof, said second width being greater than first width of said spinal implant so that said spinal implant is confined between said guide flanges of said first and second guide members.

2. The assembly of claim 1, wherein said first and second guide members each include an abutment member adjacent said distal end thereof, said abutment member projecting from said guide member in a direction opposite said guide surface.

3. The assembly of claim 2, wherein said first and second guide members each include a support member extending distally from said abutment member thereof.

4. The assembly of claim 3, wherein said guide flange of each of said first and second guide members terminates at said support member so that said support member extend distally from said guide flange of said respective guide member.

5. The assembly of claim 3, wherein said guide surface of each of said first and second guide members includes a number of guide rails extending between said proximal and distal ends thereof, and said spinal implant includes recesses in opposite surfaces thereof to receive said guide rails.

6. The assembly of claim 5, wherein said guide rails terminate at a location along said guide surface that is adjacent said abutment member.

7. The assembly of claim 6, wherein said guide surface extends distally from said guide rails along said support member and is planar along said support member.

8. The assembly of claim 1, wherein said guide surfaces are planar.

9. The assembly of claim 1, wherein said frame includes a stationary arm and a movable arm, one said first and second guide members being coupled to said stationary arm and the other of said first and second guide members being coupled to said movable arm.

10. The assembly of claim 9, wherein:
said stationary arm and said movable arm are transversely oriented to said first and second guide members; and
said frame includes a handle extending from said stationary arm.

11. The assembly of claim 1, wherein said frame portion is structured to move said guide members away from and toward one another with said guide surfaces remaining parallel to one another.

12. The assembly of claim 1, wherein said frame is transversely oriented to said first and second guide members adjacent said proximal ends of said guide members, said proximal ends of said guide members defining a proximal facing opening therebetween for receipt of said spinal implant between said guide surfaces of said first and second guide members.

* * * * *